United States Patent
Dai et al.

(10) Patent No.: US 9,670,237 B2
(45) Date of Patent: Jun. 6, 2017

(54) PHOSPHONIUM-BASED IONIC LIQUIDS AND THEIR USE IN THE CAPTURE OF POLLUTING GASES

(75) Inventors: Sheng Dai, Knoxville, TN (US); Congmin Wang, Hangzhou (CN); Huimin Luo, Knoxville, TN (US); De-en Jiang, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 1325 days.

(21) Appl. No.: 13/240,275

(22) Filed: Sep. 22, 2011

(65) Prior Publication Data

US 2013/0078170 A1   Mar. 28, 2013

(51) Int. Cl.
| | | |
|---|---|---|
| C07F 9/54 | (2006.01) |
| B01J 31/02 | (2006.01) |
| B01D 53/50 | (2006.01) |
| B01D 53/62 | (2006.01) |
| B01D 53/77 | (2006.01) |
| B01D 53/78 | (2006.01) |
| B01D 53/96 | (2006.01) |

(Continued)

(52) U.S. Cl.
CPC ........ *C07F 9/5407* (2013.01); *B01F 17/0064* (2013.01); *Y02C 10/04* (2013.01)

(58) Field of Classification Search
None
See application file for complete search history.

(56) References Cited

U.S. PATENT DOCUMENTS

| | | |
|---|---|---|
| 7,740,689 B2 | 6/2010 | Fradette et al. |
| 2005/0129598 A1 | 6/2005 | Chinn et al. |

(Continued)

FOREIGN PATENT DOCUMENTS

| | | |
|---|---|---|
| WO | WO 2005/113496 A1 | 12/2005 |
| WO | WO 2010/049739 A2 | 5/2010 |

(Continued)

OTHER PUBLICATIONS

US 7,699,910, 04/2010, Fradette et al. (withdrawn)
(Continued)

*Primary Examiner* — Daniel Berns
(74) *Attorney, Agent, or Firm* — Scully Scott Murphy & Presser

(57) ABSTRACT

An ionic liquid composition having the following chemical structural formula:

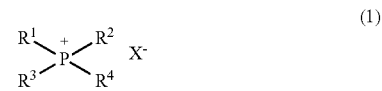

wherein $R^1$, $R^2$, $R^3$, and $R^4$ are independently selected from hydrocarbon groups containing at least 1 and up to 20 carbon atoms, and $X^-$ is a cyclic anion that possesses a negatively-charged group reactive with a gaseous electrophilic species, particularly carbon dioxide or sulfur dioxide. Methods for capturing a gaseous electrophilic species, such as $CO_2$ or $SO_2$, by contacting the gaseous electrophilic species with an ionic liquid according to Formula (1) are also described.

35 Claims, 5 Drawing Sheets

(51) Int. Cl.
B01D 53/14 (2006.01)
B01F 17/00 (2006.01)

(56) References Cited

U.S. PATENT DOCUMENTS

| | | | | |
|---|---|---|---|---|
| 2008/0265201 | A1* | 10/2008 | Spyrou | C08G 18/097 252/8.57 |
| 2009/0030158 | A1* | 1/2009 | Amano | B01J 31/0277 525/403 |
| 2009/0291874 | A1 | 11/2009 | Bara et al. | |
| 2010/0086983 | A1 | 4/2010 | Gellett et al. | |
| 2010/0203619 | A1 | 8/2010 | Fradette et al. | |
| 2012/0063978 | A1* | 3/2012 | Baugh | B01D 53/1475 423/228 |

FOREIGN PATENT DOCUMENTS

| WO | WO 2010/053377 A1 | 5/2010 |
|---|---|---|
| WO | WO 2010/078300 A1 | 7/2010 |
| WO | WO 2011/056895 A1 | 5/2011 |

OTHER PUBLICATIONS

Gurkan, B. et al., "Molecular Design of High Capacity, Low Viscosity, Chemically TUnable Ionic Liquids for CO2 Capture." J. Phys. Chem. Lett. 2010, 1, 3494-3499 (published online on Dec. 3, 2010).*
Seo et al., "Chemically Tunable Ionic Liquids with Aprotic Heterocyclic Anion (AHA) for CO2 Capture." J. Phys. Chem. B 2014, 118, 5740-5751 (published May 8, 2014).*
"3-(Trifluoromethyl)pyrazole." Sigma-Aldrich online catalog, (c) 2015. Viewed on Nov. 12, 2015 at http://www.sigmaaldrich.com/catalog/product/aldrich/406228?lang=en&region=US#.*
Wang C. et al., "Tuning the Basicity of Ionic Liquids for Equimolar $CO_2$ Capture", *Angewandte Chemie International Edition* 50(21):4918-4922 (May 16, 2011) (Published online on Mar. 2, 2011).
Smiglak M. et al., "Ionic Liquids Based on Azolate Anions", *Chemistry-A European Journal* 16(5):1572-1584 (Feb. 1, 2010).
Tsuji Y. et al., "Simple Synthesis of Tetra-n-Butylphosphonium Benzimidazolate/Benzimidazole Mixture as a Thermally Stable Proton Conductor", *Chemical Communications* 47(11):3132-3134 (Jan. 1, 2011).
Kagimoto J. et al., "Hydrophobic and Low-Density Amino Acid Ionic Liquids", *Journal of Molecular Liquids* 153(2-3):133-138 (May 15, 2010).
Jin X. et al., "Ionic Liquid High-Temperature Gas Sensor Array", *Analytical Chemistry* 78(19):6980-6989 (Oct. 1, 2006).
Fabris M. et al., "Ionic Liquids Made with Dimethyl Carbonate: Solvents as Well as Boosted Basic Catalysts for the Michael Reaction", *Chemistry-A European Journal* 15(45):12273-12282 (Nov. 16, 2009).
International Search Report and Written Opinion dated Dec. 20, 2012 received from the European Patent Office from related International Application No. PCT/US2012/056569.
Gurkan B.E. et al., "Equimolar $CO_2$ Absorption by Anion-Functionalized Ionic Liquids", *J Am. Chem. Soc.* 132(7):2116-2117 (2010).
Bates E.D. et al., "$CO_2$ Capture by a Task-Specific Ionic Liquid", *J. Am. Chem. Soc.* 124(6):926-927 (2002).
Soutullo M.D. et al., "Reversible $CO_2$ Capture by Unexpected Plastic-, Resin-, and Gel-Like Ionic Soft Materials Discovered During the Combi-Click Generation of a TSIL Library", *Chemistry of Materials* 19(15):3581-3583 (Jul. 24, 2007).
Zhang J. et al., "Supported Absorption of $CO_2$ by Tetrabutylphosphonium Amino Acid Ionic Liquids", *Chemistry-A European Journal* 12:4021-4026 (2006).
Zhang J. et al., "Dual Amino-Functionalised Phosphonium Ionic Liquids for $CO_2$ Capture", *Chemistry-A European Journal* 15:3003-3011 (2009).
Li X. et al., "Absorption of $CO_2$ by Ionic Liquid/Polyethylene Glycol Mixture and the Thermodynamic Parameters", *Green Chemistry* 10:879-884 (2008).
Gutowski K.E. et al., "Amine-Functionalized Task-Specific Ionic Liquids: A Mechanistic Explanation for the Dramatic Increase in Viscosity Upon Complexation With $CO_2$ from Molecular Simulation", *J. Am. Chem. Soc.* 130(44):14690-14704 (2008).
Fukumoto K. et al., "Room Temperature Ionic Liquids from 20 Natural Amino Acids", *J. Am. Chem. Soc.* 127(8):2398-2399 (2005).
Jessop P.G. et al., "Reversible Nonpolar-to-Polar Solvent", *Nature* 436:1102 (Aug. 25, 2005).

* cited by examiner

PHOSPHONIUM-BASED IONIC LIQUIDS AND THEIR USE IN THE CAPTURE OF POLLUTING GASES

This invention was made with government support under Prime Contract No. DE-AC05-00OR22725 awarded by the U.S. Department of Energy. The government has certain rights in the invention.

FIELD OF THE INVENTION

The present invention relates generally to methods for capturing a polluting or environmentally unfriendly gas, such as carbon dioxide or sulfur dioxide, and particularly, such methods in which an ionic liquid (IL) is employed as the capture agent.

BACKGROUND OF THE INVENTION

The emission of carbon dioxide ($CO_2$) and other polluting gases from the burning of fossil fuels has received worldwide attention because of its implication in climate change, which threatens economies and environments. Accordingly, intensive research continues in the search for new materials that can efficiently, reversibly, and economically capture $CO_2$ and other polluting gases. Ionic liquids (ILs) are particularly attractive for addressing this challenge because of their unique properties, such as low or negligible vapor pressures, wide liquid temperature ranges, generally high thermal stabilities, and tunable properties.

However, the ionic liquids thus far employed for this purpose (typically, amino-functionalized ILs) are beset with several drawbacks. A particular problem associated with many current IL capture materials is the high viscosity generated in these ILs on absorbing $CO_2$. This substantial rise in viscosity adversely slows absorption kinetics, and hence, substantially increases operating costs. There are indications that the rise in viscosity in such ILs can be attributed to strong and dense hydrogen-bond networks during the reaction of $CO_2$ with the IL (e.g., Gutowski, K. E., et al., *J. Am. Chem. Soc.*, 2008, 130, 14690-14704). Moreover, current IL materials generally possess subpar $CO_2$ absorption capacities and absorption rates for $CO_2$ capture.

SUMMARY OF THE INVENTION

In one aspect, the invention is directed to novel phosphonium ionic liquid compositions useful for capturing a gaseous electrophilic species, such as carbon dioxide or sulfur dioxide. In particular embodiments, the ionic liquid has the following chemical structural formula:

(1)

In Formula (1), $R^1$, $R^2$, $R^3$, and $R^4$ are independently selected from hydrocarbon groups containing at least 1 and up to 20 carbon atoms, and $X^-$ is a cyclic anion that possesses a negatively-charged group reactive with carbon dioxide or sulfur dioxide. Generally, $X^-$ is a deprotonated cyclic anion derived from a protic cyclic molecule X. The IL compositions described herein can advantageously maintain suitably low viscosities during gas absorption while at the same time providing high absorption capacities (e.g., significantly greater than 0.5 moles $CO_2$ per mole of IL) as well as rapid absorption rates. A particularly advantageous aspect of the IL compositions described herein is their ability to be tuned in such properties as gas absorption capacity and gas absorption rate by judicious selection of, for example, the cyclic anion ($X^-$) and substituents on the phosphonium cation (i.e., $R^1$, $R^2$, $R^3$, and $R^4$).

In another aspect, the invention is directed to methods for capturing a gaseous electrophilic species. In the method, a gas stream (from, e.g., a power plant) containing gaseous electrophilic species is contacted with at least one phosphonium ionic liquid, as described above under Formula (1). When the gaseous electrophilic species (typically, a gaseous sample containing the electrophilic species) contacts the phosphonium IL, the IL forms an addition product with the electrophilic species, typically via a covalent bond between the cyclic anion of the IL and the electrophilic species. Generally, the absorption of the electrophilic gaseous species is reversible.

DETAILED DESCRIPTION OF THE INVENTION

In a first aspect, the invention is directed to novel phosphonium ionic liquid (IL) compositions useful for capturing one or more gaseous electrophilic species. The IL compositions are conveniently described by the following generic formula:

(1)

In formula (1) above, $R^1$, $R^2$, $R^3$, and $R^4$ are each, independently, a hydrocarbon group containing at least 1 and up to 20 carbon atoms. The hydrocarbon group can be saturated or unsaturated, straight-chained or branched, and cyclic or non-cyclic. In different embodiments, the hydrocarbon groups contain at least 1, 2, 3, 4, 5, 6, 7, or 8 carbon atoms and up to 10, 12, 14, 16, 18, or 20 carbon atoms. The positive (+) charge shown in Formula (1) resides on the P atom shown in Formula 1. However, one or more additional positive charges may exist elsewhere in the phosphonium moiety adding to the overlap positive charge of the phosphonium moiety.

In a first set of embodiments, at least one, two, three, or all four of $R^1$, $R^2$, $R^3$, and $R^4$ are saturated straight-chained hydrocarbon groups (i.e., straight-chained alkyl groups). Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups.

In a second set of embodiments, at least one, two, three, or all four of $R^1$, $R^2$, $R^3$, and $R^4$ are saturated branched hydrocarbon groups (i.e., branched alkyl groups). Some examples of branched alkyl groups include isopropyl, isobutyl, sec-butyl, t-butyl, isopentyl, neopentyl, 2-methylpentyl, 3-methylpentyl, and the numerous saturated and branched hydrocarbon groups having seven and greater carbon atoms.

In a third set of embodiments, at least one, two, three, or all four of $R^1$, $R^2$, $R^3$, and $R^4$ are saturated cyclic hydrocarbon groups (i.e., cycloalkyl groups). Some examples of cycloalkyl groups include cyclopropyl, cyclobutyl, cyclopentyl, cyclohexyl, cycloheptyl, cyclooctyl, and their methyl-, ethyl-, and propyl-substituted derivatives and/or their methylene, dimethylene, trimethylene, and tetramethylene crosslinked derivatives, as crosslinked to the phosphorus atom in Formula (1). The cycloalkyl group can also be a polycyclic (e.g., bicyclic) group by either possessing a bond between two ring groups (e.g., dicyclohexyl), or by having a shared (e.g., fused) side between two or more ring groups (e.g., decalinyl, norbornyl, or adamantyl).

In a fourth set of embodiments, at least one, two, three, or all four of $R^1$, $R^2$, $R^3$, and $R^4$ are unsaturated straight-chained hydrocarbon groups (i.e., straight-chained olefinic or alkenyl groups). Some examples of straight-chained olefinic groups include vinyl, 2-propen-1-yl, 3-buten-1-yl, 2-buten-1-yl, butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl, and the numerous unsaturated and straight-chained hydrocarbon groups having eight and greater carbon atoms.

In a fifth set of embodiments, at least one, two, three, or all four of $R^1$, $R^2$, $R^3$, and $R^4$ are unsaturated branched hydrocarbon groups (i.e., branched olefinic or alkenyl groups). Some branched olefinic groups include 2-propen-2-yl, 3-buten-2-yl, 3-buten-3-yl, 4-penten-2-yl, 4-penten-3-yl, 3-penten-2-yl, 3-penten-3-yl, 2,4-pentadien-3-yl, and the numerous unsaturated and branched hydrocarbon groups having six and greater carbon atoms.

In a sixth set of embodiments, at least one, two, three, or all four of $R^1$, $R^2$, $R^3$, and $R^4$ are unsaturated cyclic hydrocarbon groups. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, cyclooctatetraenyl, and their methyl-, ethyl-, and propyl-substituted derivatives and/or their methylene, dimethylene, trimethylene, and tetramethylene crosslinked derivatives, as crosslinked to the phosphorus atom in Formula (1). The unsaturated cyclic hydrocarbon group can also be a polycyclic (e.g., bicyclic) group by either possessing a bond between two ring groups (e.g., biphenyl), or by having a shared (e.g., fused) side between two or more ring groups (e.g., naphthalenyl, anthracenyl, and phenanthrenyl).

In one embodiment, as in the examples above, one or more of the hydrocarbon groups of $R^1$, $R^2$, $R^3$, and $R^4$ are composed solely of carbon and hydrogen, i.e., do not include one or more heteroatoms, such as oxygen or nitrogen atoms. In another embodiment, one or more of the hydrocarbon groups include one or more heteroatoms, such as one or more oxygen, nitrogen, sulfur, phosphorus, and/or fluorine atoms. Some examples of oxygen-containing hydrocarbon groups include those possessing one or more hydroxyl (OH) groups, carbonyl groups (e.g., ketone, ester, amide, or urea functionalities), and/or carbon-oxygen-carbon (ether) groups. The oxygen-containing hydrocarbon group may include two or more ether groups, such as a polyalkyleneoxide group, such as a polyethyleneoxide group. Some examples of nitrogen-containing hydrocarbon groups include those possessing one or more primary amine groups, secondary amine groups, tertiary amine groups, and/or quaternary amine groups, wherein it is understood that a quaternary amine group necessarily possesses a positive charge and requires a counteranion. Some examples of fluorine-containing hydrocarbon groups (i.e., fluorocarbon groups) include the partially-substituted varieties (e.g., fluoromethyl, difluoromethyl, 2-fluoroethyl, 2,2-difluoroethyl, 2,2,2-trifluoroethyl, and the like) and perfluoro-substituted varieties (e.g., perfluoromethyl, perfluoroethyl, perfluoropropyl, perfluorobutyl, and the like). In the case of cyclic hydrocarbon groups, heteroatom substitution in the ring results in a heterocyclic ring, which may be a heterocycloalkyl, heteroalicyclic, or heteroaryl ring.

In different embodiments, two, three, or all of $R^1$, $R^2$, $R^3$, and $R^4$ are different either in structure or number of carbon atoms. In another embodiment, all of $R^1$, $R^2$, $R^3$, and $R^4$ are the same either in structure or number of carbon atoms. In particular embodiments, at least one, two, or three of $R^1$, $R^2$, $R^3$, and $R^4$ contain at least four, five, six, seven, or eight more carbon atoms than another of $R^1$, $R^2$, $R^3$, and $R^4$.

In one set of particular embodiments, the phosphonium group (i.e., $[PR^1R^2R^3R^4]^+$ group) possesses $R^1$, $R^2$, $R^3$, and $R^4$ groups that are all the same. Some examples of such phosphonium groups include tetramethylphosphonium (i.e., $P(CH_3)_4^+$), tetraethylphosphonium, tetravinylphosphonium, tetrapropylphosphonium, tetraallylphosphonium, tetrabutylphosphonium, tetrapentylphosphonium, tetrahexylphosphonium, tetracyclohexylphosphonium, tetraphenylphosphonium, tetrabenzylphosphonium, tetraheptylphosphonium, tetraoctylphosphonium, tetranonylphosphonium, tetradecylphosphonium, tetraundecylphosphonium, tetradodecylphosphonium, tetratridecylphosphonium, tetratetradecylphosphonium, tetrapentadecylphosphonium, and tetrahexadecylphosphonium. In the foregoing examples, any of the groups referred to generically (e.g., propyl, butyl, etc.) may be straight-chained (e.g., n-propyl or n-butyl) or a branched version (e.g., isopropyl, isobutyl, sec-butyl, and t-butyl).

In another set of embodiments, the phosphonium group contains a trihydrocarbyl (for example, trialkyl) moiety, wherein the hydrocarbon groups of the trihydrocarbyl moiety can be the same or different. Some examples of such phosphonium groups include ethyl(trihydrocarbyl)phosphonium, vinyl(trihydrocarbyl)phosphonium, allyl(trihydrocarbyl)phosphonium, n-propyl(trihydrocarbyl)phosphonium, isopropyl(trihydrocarbyl)phosphonium, n-butyl(trihydrocarbyl)phosphonium, isobutyl(trihydrocarbyl)phosphonium, n-pentyl(trihydrocarbyl)phosphonium, isopentyl(trihydrocarbyl)phosphonium, cyclopentyl(trihydrocarbyl)phosphonium, phenyl(trihydrocarbyl)phosphonium, benzyl (trihydrocarbyl)phosphonium, n-hexyl(trihydrocarbyl)phosphonium, isohexyl(trihydrocarbyl)phosphonium, cyclohexyl(trihydrocarbyl)phosphonium, n-heptyl(trihydrocarbyl)phosphonium, n-octyl(trihydrocarbyephosphonium, n-nonyl(trihydrocarbyl)phosphonium, n-decyl(trihydrocarbyl)phosphonium, n-undecyl(trihydrocarbyl)phosphonium, n-dodecyl(trihydrocarbyl)phosphonium, n-tridecyl(trihydrocarbyl)phosphonium, n-tetradecyl(trihydrocarbyl)phosphonium, n-pentadecyl(trihydrocarbyl)phosphonium, n-hexadecyl(trihydrocarbyl)phosphonium, n-heptadecyl(trihydrocarbyl)phosphonium, and n-octadecyl(trihydrocarbyl) phosphonium groups. In the foregoing examples, the trihydrocarbyl moiety can have hydrocarbon groups that are all the same. Some examples of such trihydrocarbyl moieties include trimethyl, triethyl, tripropyl, tributyl, tripentyl, trihexyl, triheptyl, trioctyl, trinonyl, tridecyl, tri(dodecyl), tri(tridecyl), tri(tetradecyl), trivinyl, triallyl, triphenyl, tribenzyl, tricyclopentyl, and tricyclohexyl moieties. Alternatively, the trihydrocarbyl moiety can have at least two hydrocarbon groups that are different. Some examples of such trihydrocarbyl moieties include ethyldimethyl, diethylmethyl, dimethylpropyl, methyldipropyl, ethyldipropyl, diethylpropyl, butyldimethyl, dibutylmethyl, butyldiethyl, dibutylethyl, dimethylpentyl, methyldipentyl, diethylpentyl, dipropylpentyl, dimethylphenyl, dimethylcyclopentyl, dicyclopentylmethyl, octyldimethyl, methyldioctyl, decyldimethyl, didecylmethyl, didecylethyl, dodecyldimethyl, tridecyldimethyl, tetradecyldimethyl, hexadecyldimethyl, dimethylphenyl, diethylphenyl, methyldiphenyl, and dimethylbenzyl moieties. In the foregoing examples, any of the groups referred to generically (e.g., propyl, butyl, etc.) may be straight-chained (e.g., n-propyl or n-butyl) or branched (e.g., isopropyl, isobutyl, sec-butyl, and t-butyl).

In another set of embodiments, the phosphonium group contains a (dihydrocarbyl) (for example, dialkyl) moiety, wherein the groups of the (dihydrocarbyl) moiety can be the same or different. Some examples of such phosphonium groups include diethyl(dihydrocarbyl)phosphonium, divinyl(dihydrocarbyl)phosphonium, dipropyl(dihydrocarbyl)phosphonium, dibutyl(dihydrocarbyl)phosphonium, dipentyl(dihydrocarbyl)phosphonium, dicyclopentyl(dihydrocarbyl)phosphonium, dihexyl(dihydrocarbyl)phosphonium, dicyclohexyl(dihydrocarbyl)phosphonium, diphenyl(dihydrocarbyl)phosphonium, diheptyl(dihydrocarbyl)phosphonium, dioctyl(dihydrocarbyl)phosphonium, dinonyl(dihydrocarbyl)phosphonium, didecyl(dihydrocarbyl)phosphonium, diundecyl(dihydrocarbyl)phosphonium, didodecyl(dihydrocarbyl)phosphonium, ditridecyl(dihydrocarbyl)phosphonium, ditetradecyl(dihydrocarbyl)phosphonium, dipentadecyl(dihydrocarbyl)phosphonium, dihexadecyl(dihydrocarbyl)phosphonium, diheptadecyl(dihydrocarbyl)phosphonium, and dioctadecyl(dihydrocarbyl)phosphonium groups. In the foregoing examples, the dihydrocarbyl moiety can have hydrocarbon groups that are all the same. Some examples of such dihydrocarbyl moieties include dimethyl, diethyl, dipropyl, dibutyl, dipentyl, dihexyl, diheptyl, dioctyl, dinonyl, didecyl, di(dodecyl), di(tridecyl), di(tetradecyl), divinyl, diallyl, diphenyl, dibenzyl, dicyclopentyl, and dicyclohexyl moieties. Alternatively, the dihydrocarbyl moiety can have hydrocarbon groups that are different. Some examples of such dihydrocarbyl moieties include ethylmethyl, methylpropyl, butylmethyl, methylpentyl, methylphenyl, methylbenzyl, methylcyclopentyl, methyloctyl, methylnonyl, methyldecyl, methyldodecyl, and methyltetradecyl moieties, as well as dihydrocarbyl moieties wherein the methyl group of the foregoing examples is replaced with ethyl, propyl, isopropyl, n-butyl, sec-butyl, isobutyl, or t-butyl. In the foregoing examples, any of the groups referred to generically (e.g., propyl, butyl, etc.) may be straight-chained (e.g., n-propyl or n-butyl) or branched (e.g., isopropyl, isobutyl, sec-butyl, and t-butyl).

In some embodiments, the phosphonium group described above can be a diphosphonium or triphosphonium group. Formula (1), above, encompasses diphosphonium and triphosphonium groups when one or two of $R^1$, $R^2$, $R^3$, and $R^4$ are heteroatom-substituted with a phosphorus atom to incorporate one or two additional phosphonium groups. It is understood that charge neutrality must exist between the phosphonium moiety and anion shown in Formula (1). Thus, if the phosphonium moiety in Formula (1) is a diphosphonium moiety with a +2 charge, the diphosphonium moiety is complexed with two of $X^-$ if $X^-$ is a monoanion, or one of $X^-$ if $X^-$ is a dianion (i.e., $X^{2-}$). Some examples of diphosphonium moieties include mono- or di-alkylated versions of dmpe, such as ethylene-1,2-bis(trimethylphosphonium); mono- or di-alkylated versions of dppe, such as ethylene-1,2-bis(methyldiphenylphosphonium); as well as mono- or di-alkylated versions of 2,2'-bis(dicyclohexylphosphino)-1,1'-biphenyl, 2,2'-bis(diphenylphosphino)-1,1'-biphenyl, 2,2'-bis(di-t-butylphosphino)-1,1'-biphenyl, 2,2'-bis(diphenylphosphino)-1,1'-binaphthyl (i.e., BINAP), 1,3-bis(di-t-butylphosphinomethyl)benzene, and 2-(di-t-butylphosphino)biphenyl. In some embodiments, the phosphonium moiety (i.e., $[PR^1R^2R^3R^4]^+$) in Formula (1) encompasses only monophosphonium moieties, and does not include diphosphonium, triphosphonium, or polyphosphortium moieties.

Typically, $R^1$, $R^2$, $R^3$, and $R^4$ groups are not interconnected. However, in some embodiments, two, three, or all of $R^1$, $R^2$, $R^3$, and $R^4$ can be interconnected, thereby resulting in a cyclic phosphonium moiety. Some examples of cyclic phosphonium moieties are the P-dialkylated phosphinanes (P-dialkylated phosphacyclohexanes), such as 1,1-dihydrocarbylphosphorinanium moieties (e.g., 1-benzyl-1-phenylphosphorinanium and 1,1-diphenyl-4-methylphosphorinanium), the salts of which are commercially available or can be prepared by known preparative methods.

The cyclic anion group $X^-$ (i.e., "cyclic anion") possesses at least one negatively-charged group reactive with a gaseous electrophilic species, such as carbon dioxide or sulfur dioxide. By being reactive with the gaseous electrophilic species is generally meant herein that the negatively-charged group nucleophilicly attacks and forms a covalent bond with an electrophilic atom of the gaseous electrophilic species, e.g., the carbon atom of carbon dioxide or the sulfur atom of sulfur dioxide. The negatively-charged group can be, for example, a deprotonated organoamine, deprotonated hydroxy, or deprotonated thiol group. The deprotonated organoamine group considered herein is generally derived from a secondary organoamine group that is part of the ring structure (i.e., a ring atom) of the cyclic anion, as in, e.g., N-deprotonated piperidine or oxazolidine as the cyclic anion. However, the deprotonated organoamine group may, alternatively, be derived from a primary or secondary organoamine group that is attached to the ring (i.e., as a substituent attached to a ring atom), as in, e.g., N-deprotonated forms of aniline, N-methylaniline, benzamide, or N-methylbenzamide as the cyclic anion. The deprotonated hydroxy group can be, for example, a phenoxide (i.e., derived from the deprotonation of a phenol) or alkoxide (derived from the deprotonation of, e.g., a hydroxyalkyl group attached to the ring of the cyclic anion). A deprotonated thiol group is analogous to the deprotonated hydroxy group, except that sulfur replaces oxygen in the hydroxy group.

Some negatively-charged groups that do not react with an electrophilic gaseous species (i.e., non-reactive negatively-charged groups), in the meaning described above, include, for example, carboxylate, sulfonate, nitro, and phosphonate groups. In some embodiments, non-reactive negatively-charged groups can be included in the cyclic anion as long as the cyclic anion also includes a reactive negatively-charged group, and the non-reactive negatively-charged group does not interfere with the function, as described above, of the reactive negatively-charged group. In other embodiments, some or all non-reactive negatively-charged groups are excluded from the cyclic anion. In some embodiments, the negatively-charged group is a ring atom, as in N-deprotonated piperidine. Typically, when the negatively-charged group is a ring atom, a negatively-charged substituent is not also attached to the ring. In some embodiments, the negative charge of the cyclic anion resides only at one or more ring atoms, i.e., without any negatively-charged substituent attached to the ring. In such embodiments, cyclic anions containing negatively-charged substituents, such as piperidine-2-carboxylate, piperidine-3-carboxylate, 2-hydroxypiperidine (O-deprotonated), 3-hydroxypiperidine (O-deprotonated), and proline (carboxy-deprotonated), are excluded.

In particular embodiments, the cyclic anion ($X^-$) is an anionic form of a heterocyclic molecule. Typically, the heterocyclic anion is a deprotonated form of a heterocyclic molecule, particularly where the deprotonation occurs at a heteroatom in the ring. For example, the heterocyclic anion may be a deprotonated form of a heterocyclic molecule containing one, two, or more secondary amine (NH) groups defining the ring (i.e., NH ring groups), wherein one or more of the NH ring groups are deprotonated to form a negatively-charged nitrogen atom in the ring. In some embodiments, the heterocyclic anion is saturated, i.e., $X^-$ is heteroalicyclic. Some examples of heteroalicyclic anions containing one ring nitrogen atom include N-deprotonated forms of pyrrolidine, 2-pyrrolidone (i.e., 2-pyrrolidinone), piperidine, morpholine, thiomorpholine, oxazolidine, thiazolidine, and azepane. Some examples of heteroalicyclic anions containing two ring nitrogen atoms include N-deprotonated forms of imidazolidine, piperazine, pyrazolidine, hexahydropyrimidine, and hexahydropyridazine. In other embodiments, the heterocyclic anion is unsaturated while containing at least one deprotonated NH group. The unsaturated heterocyclic anion may be, for example, a heteroaliphatic or heteroaromatic anion. Some examples of unsaturated heterocyclic anions containing at least one deprotonated NH group include N-deprotonated forms of pyrrole, indole, indoline, benzimidazole, purine, and the pyrimidine nucleobases (e.g., cytosine and uracil).

In other embodiments, the cyclic anion ($X^-$) contains a reactive anionic group as a substituent on a ring, wherein the ring may be heterocyclic or non-heterocyclic. Some examples of such cyclic anions include deprotonated forms of phenolic or thiophenolic compounds, such as O-deprotonated forms of phenol, o-, m-, or p-cresol, the xylenols (e.g., 2,6-dimethylphenol), 2-, 3-, or 4-aminophenol, resorcinol, 2-hydroxypyridine, 2-hydroxyquinoline, 4-hydroxyquinazoline, and S-deprotonated forms of thiophenol and the thiocresols.

In some embodiments, the cyclic anion ($X^-$) is not an amino acid, such as proline, histidine, tryptophan, or tyrosine. However, derivatized versions of such cyclic amino acids may be considered for the cyclic anion if the carboxy group therein is not in a charged deprotonated form, such as when the carboxy group is esterified or replaced by a non-charged group.

The cyclic anion should have sufficient basicity (i.e., nucleophilicity) to react with the electrophilic species in the manner described above. Thus, the cyclic anion ($X^-$) is preferably derived from a protic molecule X having a $pK_a$ of at least 5 in water at 25° C. In different embodiments, the cyclic anion is derived from a protic molecule X having a $pK_a$ of about, at least, or above 5, 6, 7, 8, 9, 10, 11, 12, 13, or 14 in water at 25° C.

The combination of phosphonium moiety ($[PR^1R^2R^3R^4]^+$) and cyclic anion ($X^-$), shown in Formula (1) results in an ionic liquid. The ionic liquids of the invention according to Formula (1) are generally in liquid form (i.e., fluids) at or below 100° C., more preferably at or below 50° C., and even more preferably, at or below room temperature (i.e., at or less than about 15, 20, 25, or 30° C.). In other embodiments, the ionic liquids are in liquid form at or below 0° C., −5° C., −10° C., −20° C., or −30° C. Preferably, the ionic liquid possesses a melting (or fusion) point (i.e., $T_{fus}$) that is at or below any of the temperatures given above. Although the invention primarily contemplates ionic liquids that are naturally fluids at or below room temperature, the invention also contemplates ionic liquids that are solid or semi-solid at about room temperature or above, but which can be rendered liquids at a higher temperature by the application of heat. The latter embodiment may be particularly suitable if the gas absorption process is conducted at a temperature above room temperature.

Generally, the density of the ionic liquid according to Formula (1) is above 1.2 g/mL at an operating temperature of interest, and particularly at a temperature within 20-30° C. In different embodiments, the density of the ionic liquid is about or at least 1.2, 1.3, 1.4, 1.5, 1.6, 1.7, or 1.8 g/mL, or within a range bounded by any two of these values.

The viscosity ($\eta$) of the ionic liquid according to Formula (1) is preferably no more than 50,000 centipoise (50,000 cP) at an operating temperature of interest, and particularly at a temperature within 20-30° C. or about 25° C. In more preferred embodiments, the viscosity of the ionic liquid is no more than or less than about 25,000 cP, 10,000 cP, 5,000 cP, 2,000 cP, 1,500 cP, 1,000 cP, 800 cP, 700 cP, 600 cP, 500 cP, 400 cP, 300 cP, 250 cP, 200 cP, 150 cP, 100 cP, or 50 cP at a temperature of about 25° C., or the viscosity is within a particular range bounded by any two of the foregoing exemplary values.

The conductivity ($\sigma$) of the ionic liquid according to Formula (1) is generally at least 0.5 µS/m at an operating temperature of interest, and particularly at a temperature within 20-30° C. In different embodiments, the conductivity of the ionic liquid may be at least 0.5, 1.0, 1.5, 2.0, 2.5, 3.0, 3.5, 4.0, 4.5, or 5.0 µS/m, or within a particular range bounded by any two of the foregoing exemplary values.

The ionic liquid according to Formula (1) preferably possesses a decomposition temperature ($T_{dec}$) of at least 150° C. In different embodiments, the decomposition temperature is at least 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C., or within a particular range bounded by any two of the foregoing exemplary values.

The ionic liquid according to Formula (1) preferably possesses an electrophilic gas (e.g., $CO_2$ or $SO_2$) absorption capacity of at least 0.5 moles of the electrophilic gas per mole of the ionic liquid. In different embodiments, the electrophilic gas absorption capacity is at least or above 0.5, 0.6, 0.7, 0.8, 0.9, 0.95, 1.00, or 1.05 moles of the electrophilic gas per mole of the ionic liquid. In some embodiments, the electrophilic gas absorption capacity is about 1 mole of electrophilic gas per mole of the ionic liquid.

The ionic liquid can be of any suitable purity level. Preferably, the ionic liquid has a purity at least or greater than 95%, 96%, 97%, 98%, 99%, 99.5%, or 99.9%. The ionic liquid is preferably substantially devoid of salt byproducts that are typically produced during synthesis of the ionic liquid. In preferred embodiments, it is desirable that the ionic liquid contains less than 1% by weight of salt byproducts, and more preferably, less than 0.5%, 0.1%, 0.01%, or even 0.001% by weight of salt byproducts.

As used herein, the term "about" generally indicates no more than ±10% of a given value, and more generally within ±0.5, 1, 2, or 5% of a given value. For example, in its broadest sense, "about 25° C." can mean 25° C.±10%, which indicates 25±2.5° C. or 22.5-27.5° C.

The ionic liquids described above can be produced by any suitable method. By a preferred method, the ionic liquids described above are produced by reacting a phosphonium hydroxide precursor compound of the formula $[PR^1R^2R^3R^4]^+OH^-$ (wherein $R^1$, $R^2$, $R^3$, and $R^4$ have the meanings provided above under Formula (1)) with a proton donor compound X, which becomes deprotonated to the cyclic anion $X^-$ with simultaneous formation of water. The phosphonium hydroxide can, in turn, be prepared from the corresponding phosphonium halide, e.g., $[PR^1R^2R^3R^4]^+$ $[Y^-]$, where $Y^-$ typically represents $Cl^-$, $Br^-$, or $I^-$, by methods known in the art (e.g., the anion-exchange method taught in Fukumoto, K., et al., *J. Am. Chem. Soc.*, 2005, 127, 2398-2399). The phosphonium halide precursor can, in turn, be produced by methods well known in the art, such as by the reaction of a phosphine precursor $[PR^1R^2R^3]$ with an alkylating agent $[R_4]^+[Y]^-$.

The foregoing methodology is generally depicted, as follows, with imidazole as the compound X.

The synthesis is preferably conducted in a polar solvent, such as an alcohol, e.g., ethanol. Solvent and produced water can then be removed by, for example, distillation. If desired, the ionic liquid may be further purified, such as by distillation. Other methods may be used to prepare the ionic liquids described herein. For example, a phosphonium salt precursor compound of the formula $[PR^1R^2R^3R^4]^+Y^-$ (wherein $R^1$, $R^2$, $R^3$, and $R^4$ have the meanings provided above under Formula (1)) and $Y^-$ is a counteranion, such as a halide (e.g., $Cl^-$, $Br^-$, or $I^-$), can be reacted with a salt form of the cyclic anion (e.g., sodium imidazolate) to form the phosphonium imidazolate with simultaneous formation of a byproduct salt of $Y^-$, such as $Na^+Y^-$.

The invention is also directed to a liquid gas-absorption medium (i.e., gas absorption medium) useful for removing (i.e., by scrubbing) polluting gas from a gas stream (gaseous effluent). The gas absorption medium contains at least one ionic liquid according to Formula (1).

In one embodiment, the gas absorption medium contains solely one or a combination of ionic liquids according to Formula (1). In another embodiment, the gas absorption medium contains one or more ionic liquids according to Formula (1) in admixture with one or more components that are not ionic liquids. The one or more components that are not ionic liquids may be, for example, a solvent in which the ionic liquid is dissolved or dispersed, an electrolyte salt, a viscosity modifier, a surfactant, or a defoamer. In other embodiments, the gas absorption medium is completely or substantially devoid of any one or more of the foregoing additional components other than one or more ionic liquids according to Formula (1).

In some embodiments, the gas absorption medium includes one or more non-ionic liquids (e.g., one or more solvents). The non-ionic liquid can be, for example, a polar protic, polar non-protic, or non-polar solvent. The solvent may be included in an amount of, or at least, or less than, for example, 0.1 wt %, 0.5 wt %, 10 wt %, 20 wt %, 30 wt %, 40 wt %, 50 wt %, 60 wt %, 70 wt %, 80 wt %, 90 wt % by total weight of the gas absorption medium, or within a range bounded by any two of the foregoing values.

In the case of a polar protic solvent, it may be included as long as it does not protonate the negatively-charged group present on the cyclic anion. Some examples of polar protic solvents include water, the alcohols (e.g., methanol, ethanol, isopropanol, n-butanol, t-butanol, the pentanols, hexanols, octanols, or the like), diols (e.g., ethylene glycol, diethylene glycol, triethylene glycol), polyols, polyethyleneglycols, and protic amines (e.g., ethylenediamine, ethanolamine, diethanolamine, and triethanolamine). Some examples of polar non-protic solvents include the nitriles (e.g., acetonitrile, propionitrile), sulfoxides (e.g., dimethylsulfoxide), amides (e.g., dimethylformamide, N, N-dimethylacetamide), organochlorides (e.g., methylene chloride, chloroform, 1,1,-trichloroethane), ketones (e.g., acetone, 2-butanone), dialkylcarbonates (e.g., ethylene carbonate, dimethylcarbonate, diethylcarbonate), organoethers (e.g., diethyl ether, tetrahydrofuran, and dioxane), HMPA, NMP, and DMPU. Some examples of non-polar solvents include the liquid hydrocarbons, such as a pentane, hexane, heptane, octane, pentene, hexene, heptene, octene, benzene, toluene, or xylene. In some embodiments, one or more of any of the foregoing classes or specific types of non-ionic liquids are excluded from the gas absorption medium.

In some embodiments, it may be preferable to exclude from the gas absorption medium non-ionic liquids having a boiling point under 25° C., 50° C., or 100° C. In other embodiments, it may be preferable to include or exclude from the gas absorption medium non-ionic liquids having a boiling point over 100° C., 150° C., 200° C., or 250° C. In other embodiments, it may be preferable to include or exclude non-ionic liquids having a molecular weight of or greater than 200, 300, 400, 500, 1000, 1500, 2000, or 5000 g/mol. In yet other embodiments, it may be preferable to include a non-ionic liquid in which the ionic liquid is substantially soluble, or partially soluble, or substantially insoluble (e.g., as separate phases).

In one embodiment, the gas absorption medium (and hence, the ionic liquid by itself) is substantially devoid of water. By being "substantially devoid" of water is meant that the gas absorption medium or ionic liquid contains less than 0.5%, 0.1%, or 0.01% by weight of water (i.e., wt %) with respect to the total weight of gas absorption medium, or by weight of the ionic liquid and water. In a particular embodiment, the gas absorption medium or ionic liquid is completely devoid of water (i.e., dry) such that any water present is less than 0.001 wt %.

In another embodiment, the gas absorption medium (or ionic liquid by itself) contains an amount of water. In different embodiments, the amount of water can be about, less than, or at least, for example, 1 wt %, 2 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, or 97 wt % of water by total weight of the gas absorption medium or by weight of the ionic liquid and water, or within a range bounded by any two of the foregoing values.

The gas absorption medium may include one or more electrolyte salts, as long as the electrolyte salt does not interfere with the ability of the ionic liquid to capture an electrophilic gas. Some examples of electrolyte salts or acids include the fluoride-containing electrolytes (e.g., HF, KF, LiF, NaF, $NH_4F$, or a tetraalklyammonium fluoride, such as $Bu_4NF$), chloride-containing electrolytes (e.g., HCl, KCl, NaCl, $NH_4Cl$, or a tetraalklyammonium chloride, such as $Et_4NCl$), bromide-containing salts (e.g., HBr, KBr, NaBr, $NH_4Br$, or a tetraalklyammonium bromide, such as $Bu_4NBr$), ammonium salts, nitrate salts (e.g., $LiNO_3$, $NaNO_3$, $KNO_3$, and $Mg(NO_3)_2$), nitrite salts, phosphate salts, phosphite salts, alkylphosphate salts, phosphinate salts, sulfate salts, alkylsulfate salts, carboxylate salts (e.g., sodium glycolate, sodium acetate, sodium propionate, potassium oxalate), carbonate salts, bicarbonate salts, perchlorate salts, chlorate salts, perbromate salts, and bromate salts. In some embodiments, one or more classes or specific types of the electrolyte salts described above, or all electrolyte salts, are excluded from the gas absorption medium.

The gas absorption medium may also include one or more surfactants, as long as the surfactant does not interfere with the ability of the ionic liquid to capture an electrophilic gas. The surfactants can be included to, for example, modify or adjust the gas absorption kinetics during a gas processing operation. In other embodiments, one or more (or all) surfactants are excluded from the gas absorption medium.

In another aspect, the invention is directed to methods for capturing a gaseous electrophilic species from a gaseous effluent using the above-described gas absorption medium containing one or a combination of ionic liquids described above. Generally, in order to establish efficient contact with the gaseous effluent, the gaseous effluent is bubbled through the gas absorption medium. If desired, to establish more intimate contact between the ionic liquid and gas, the gas absorption medium can be agitated while the gas is bubbled through (e.g., by stirring or shaking), or by diminishing the size of the gas bubbles (by, for example, passing the gas bubbles through a sieve, mesh plate, or other gas-dispersing element, or by use of a gas-dissolution additive).

The gaseous electrophilic species considered herein are able to react with and form a covalent bond with a suitably reactive anionic group, such as a deprotonated organoamine group (i.e., bearing a negatively-charged nitrogen atom) or deprotonated alcohol group (i.e., alkoxide or phenoxide) contained in the cyclic anion ($X^-$) of the ionic liquid according to Formula (1). Typically, the electrophilic species is a gaseous oxide compound, such as carbon dioxide ($CO_2$) and sulfur dioxide ($SO_2$). Other electrophilic species include, for example, sulfur trioxide ($SO_3$), carbon monoxide (CO), nitrogen dioxide ($NO_2$), and selenium dioxide ($SeO_2$). Generally, the electrophilic species considered herein is a toxic or polluting species that is desirably removed (preferably, selectively) from the environment. The electrophilic species is typically in the form of a gas; however, in some embodiments, the electrophilic species may be a liquid (or converted into a liquid) before contacting the ionic liquid.

The electrophilic gas reacts with the cyclic anion portion of the ionic liquid described above by forming a covalent bond (generally, reversible or weak covalent bond) between the negatively-charged portion of the cyclic anion and an electrophilic atom of the electrophilic gas. By the instant methodology, the electrophilic gas generally does not become protonated during the reaction, thereby allowing for more facile recovery of the electrophilic gas.

Typically, in order for the ionic liquid to be re-used, the electrophilic gas is stripped from the IL-gas addition product. The electrophilic gas can be separated from the IL-gas product by, for example, elevating the temperature and/or lowering the atmospheric pressure of the gas absorption medium. The separated electrophilic gas can then be directed into a storage facility, or further processed. For efficient storage, the gas is generally concentrated by, for example, suitable pressurization and/or cooling. In other embodiments, the separated gas is reacted with one or more compounds to produce a liquid or solid compound that can be more conveniently stored or used as a feedstock or final end-product.

The invention is particularly directed to an arrangement in which the method, described above, for capturing an electrophilic gas is integrated with a process that produces the electrophilic gas as a byproduct. The process is typically an industrial process, such as a combustion process (e.g., in the burning of a combustible, such as wood or a fossil fuel, such as coal or petroleum, typically for generation of electrical power) or a chemical production process. By being integrated, a gas effluent emanating from the industrial process is directed into a gas absorption medium used in the gas scrubbing process described above. In some embodiments, the integration provides a continuous process in which gaseous effluent (e.g., a flue gas) is continuously processed by reacting with the gas absorption medium described above, followed by removal (desorption) of the electrophilic gaseous species to regenerate the ionic liquid, and cycling of the regenerated ionic liquid back to the gas effluent stream to remove more electrophilic gas therefrom.

A particular advantage of the ionic liquids described herein is their resistance to an increase in viscosity during absorption of the gaseous electrophilic species. The instant ionic liquids are particularly resistant to the phenomenon, often encountered in the art, of forming highly viscous gels or solids during absorption of a gaseous electrophilic species. In preferred embodiments, the ionic liquids described herein may display a rise in viscosity of no more than, for example, 1000 cP, 900 cP, 800 cP, 700 cP, 600 cP, 500 cP, 400 cP, 300 cP, 200 cP, or 100 cP during the course of gas absorption, and in preferred embodiments, even after complete absorption for the IL is achieved. In some embodiments, the viscosity is substantially maintained or may even decrease.

Examples have been set forth below for the purpose of illustration and to describe certain specific embodiments of the invention. However, the scope of this invention is not to be in any way limited by the examples set forth herein.

EXAMPLE 1

Preparation and Characterization of Ionic Liquid Compositions

Introduction

Figure 1:
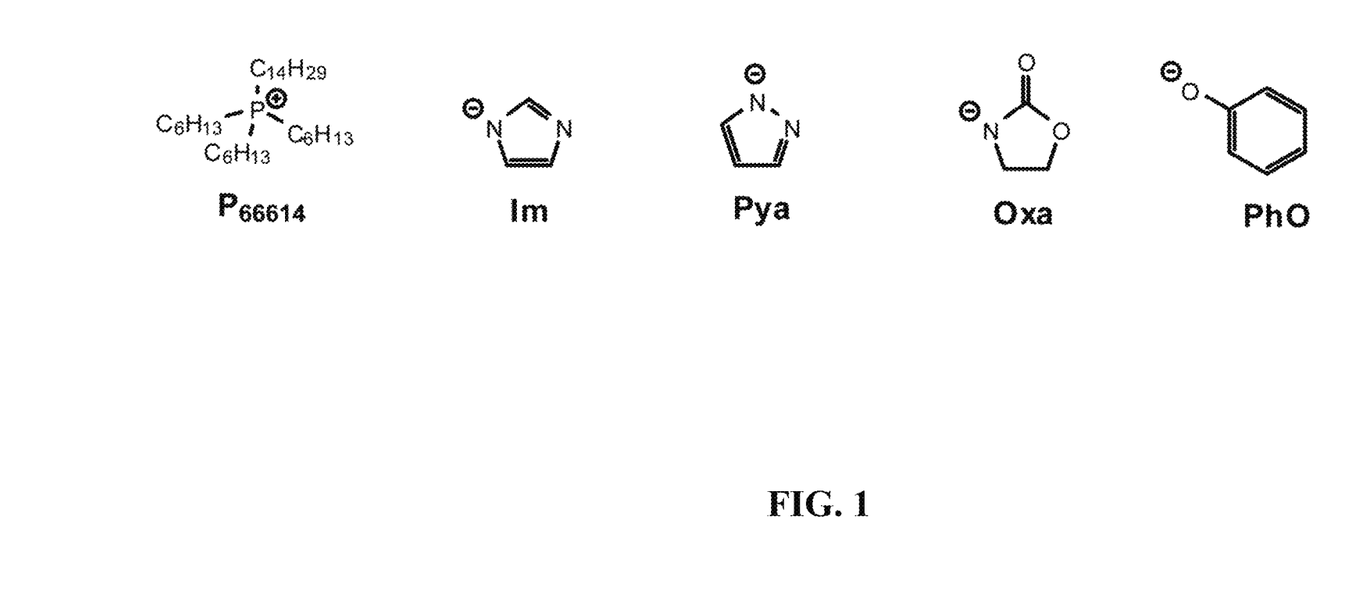
FIG. 1. Structures of $P_{66614}$ and cyclic anions Im (deprotonated imidazole), Pyr (deprotonated pyrazole), Oxa (deprotonated oxazolidinone), and PhO (deprotonated phenol).

Four representative IL compositions were prepared and investigated. The four IL compositions are within the formula [$P_{66614}^+$][$X^-$], wherein $P_{66614}$ indicates trihexyl(tetradecyl)phosphonium and $X^-$ is specified as N-deprotonated imidazole (Im), N-deprotonated oxazolidinone (Oxa), N-deprotonated pyrazole (Pyr), and O-deprotonated phenol (PhO) in accordance with the definition provided under Formula (1). The four IL compositions are identified as: [$P_{66614}$][Im], [$P_{66614}$][Oxa], [$P_{66614}$][Pyr], and [$P_{66614}$][PhO]. The structures of the foregoing ionic liquid compositions are explicitly shown in FIG. 1. The $pK_a$ values in water for imidazole, oxazolidinone, and phenol are 14.5, 12.0, and 10.0, respectively.

Synthesis

The four exemplary ILs were generally prepared by neutralizing trihexyl(tetradecyl)-phosphonium hydroxide ([$P_{66614}$][OH]) with a weak proton donor, such as imidazole. A solution of [$P_{66614}$][OH] in ethanol was prepared from [$P_{66614}$][Br] using an anion-exchange resin by methods known in the art (e.g., the anion-exchange method taught in Fukumoto, K., et al., 2005, Ibid.). An equimolar amount of imidazole was added into the [$P_{66614}$][OH] solution in ethanol. The mixture was stirred at room temperature for about 12 hours. Subsequently, ethanol and water were removed by distillation at 60° C. The obtained product was dried under high vacuum for 24 hours at 60° C. The structures of these ILs were confirmed by NMR and IR. No impurity was found by NMR. The water content of these ILs was determined by a Karl Fisher titration and found to be less than 0.1 wt %. The residual bromide content of these ILs was determined by a semi-quantitative Nessler cylinder method (A. Stark, et al., *Green Chem.*, 10, 1152 (2008)) which showed that the bromide content was lower than 0.15 wt %.

Characterization

[$P_{66614}$][Im]: $^1$H NMR (CDCl$_3$): 0.90 ( m, 12H, CH$_3$), 1.30-1.56 (m, 48H, CH$_2$), 2.36 (m, 8H, PCH$_2$), 7.07 (s, 2H, Im C4 and C5), 7.68 ppm (s, 1H, Im C2); $^{13}$C NMR (CDCl$_3$): 13.8, 14.0, 21.7, 22.2, 22.5, 28.8, 29.2, 29.3, 29.5, 30.2, 30.4, 30.6, 30.7, 30.9, 31.8, 121.5, 135.2 ppm; IR: 2955, 2922, 2853, 2363, 2340, 2133, 1580, 1466, 1298, 1246, 1213, 1151, 1072, 986, 918, 816, 756, 721, 685, 667 cm$^{-1}$.

[$P_{66614}$][Oxa]: $^1$H NMR (CDCl$_3$): 0.88 (m, 12H, CH$_3$), 1.26-1.67 (m, 48H, CH$_2$), 2.43 (m, 8H, PCH$_2$), 3.65 (m, 2H, Oxa), 4.40 ppm (m, 2H, Oxa); $^{13}$C NMR (CDCl$_3$): 13.7, 13.9, 18.8, 19.2, 21.7, 22.2, 22.5, 28.8, 29.1, 29.3, 29.4, 30.2, 30.3, 30.9, 31.7, 40.5, 64.5, 160.0 ppm; IR: 2955, 2922, 2855, 1751, 1653, 1628, 1458, 1377, 1275, 1240, 1161, 1084, 1030, 957, 910, 800, 766, 719 cm$^{-1}$.

[$P_{66614}$][PhO]: $^1$H NMR (CDCl$_3$): 0.88 (m, 12H, CH$_3$), 1.22-1.46 (m, 48H, CH$_2$), 2.29 (m, 8H, PH$_2$), 6.71 (m, 1H, C4), 7.01 (d, 2H, C2 and C6), 7.11 ppm (m, 2H, C3 and C5); $^{13}$C NMR (CDCl$_3$): δ=13.7, 13.9, 18.4, 19.1, 21.7, 22.2, 22.5, 28.8, 29.2, 29.5, 30.2, 30.3, 30.5, 30.9, 1.7, 115.9, 117.9 128.5, 158.5 ppm; IR: 2957, 2924, 2855, 2364, 2341, 1581, 1559, 1485, 1467, 1306, 1156, 1105, 1054, 983, 859, 823, 754, 720 cm$^{-1}$.

Various other properties of the four exemplary ILs described above are provided in Table 1 below.

TABLE 1

Properties of the four exemplary ionic liquids

| ILs | $T_{fus}$/° C. | $T_{dec}$/° C. | η/cP | σ/μS · m$^{-1}$ |
|---|---|---|---|---|
| [$P_{66614}$][Im] | −60 | 252 | 810.4 | 2.65 |
| [$P_{66614}$][Oxa] | −64 | 224 | 555.1 | 1.42 |
| [$P_{66614}$][PhO] | −67 | 263 | 390.3 | 1.58 |
| [$P_{66614}$][Pyr] | −68 | 182 | 245.4 | 2.50 |

In Table 1 above, $T_{fus}$ is the temperature of fusion measured by differential scanning calorimetry (DSC), $T_{dec}$ is the decomposition temperature corresponding to a 10% mass loss measured using thermogravimetric analysis (TGA), η is the viscosity measured at 25° C., and σ is the ionic conductivity measured at 23° C.

As shown by Table 1, TGA revealed that all of these ILs were stable up to at least 180° C., and [$P_{66614}$][Im] showed a particularly high decomposition temperature of more than 250° C. Table 1 also shows that the viscosities of these ILs are strongly affected by the anion, with [$P_{66614}$][Pyr] showing a particularly low viscosity of 245.4 cP.

EXAMPLE 2

Carbon Dioxide Absorption Experiments

In a typical CO$_2$ absorption experiment, CO$_2$ at atmospheric pressure was bubbled through approximately 1.0 g of the IL in a glass container having an inner diameter of about 10 mm at a flow rate of about 60 ml/min. During the experiment, the glass container was partly immersed in an oil bath at the desired temperature. The amount of CO$_2$ absorbed was determined at regular intervals by an electronic balance with an accuracy of ±0.1 mg. Absorbed CO$_2$ was released by heating under bubbling N$_2$ gas.

NMR and IR data is provided, as follows, on the ILs after they absorbed CO$_2$ (i.e., on the ILs complexed with CO$_2$). The designations TmC, OxaC, PyrC, and PhOC all indicate complexation of CO$_2$ with the respective cyclic anions Im, Oxa, Pyr, and PhO.

After the absorption of CO$_2$ for [$P_{66614}$][ImC]: $^1$H NMR (CDCl$_3$): 0.88 (m, 12H, CH$_3$), 1.24-1.66 (m, 48H, CH$_2$), 2.28 (m, 8H, PCH$_2$), 7.02 (s, 2H, Im C4 and C5), 7.66 ppm (s, 1H, Im C2); $^{13}$C NMR (CDCl$_3$): 13.6, 13.8, 18.4, 18.9, 21.4, 22.0, 28.9, 29.0, 29.2, 29.3, 30.0, 30.2, 30.7, 122.5, 135.5, 163.0 ppm; IR: 2955, 2924, 2855, 2363, 2338, 1711, 1626, 1466, 1377, 1281, 1169, 1063, 1043, 982, 907, 835, 816, 803, 768, 721, 690, 665 cm$^{-1}$.

After the absorption of CO$_2$ for [$P_{66614}$][OxaC]: $^1$H NMR (CDCl$_3$): 0.88 (m, 12H, CH$_3$), 1.26-1.54 (m, 48H, CH$_2$), 2.38 (m, 8H, PCH$_2$), 3.63 (m, 2H, Oxa), 4.37 ppm (m, 2H, Oxa); $^{13}$C NMR (CDCl$_3$): 13.9, 14.0, 18.8, 19.3, 21.9, 22.3, 22.7, 28.9, 29.3, 29.5, 29.6, 30.4, 30.5, 31.1, 31.9, 40.7, 64.7, 160.3 ppm; IR: 2955, 292, 2853, 1751, 1655, 1458, 1377, 1246, 1165, 1086, 1016, 934, 818, 766, 721 cm$^{-1}$.

During the capture of CO$_2$, the four exemplary ILs reacted with CO$_2$ to form a liquid carbamate or carbonate salt, which was verified by NMR and IR. For example, as shown by the above IR results, compared with fresh IL [$P_{66614}$][Im], a new peak at 1711 cm$^{-1}$, attributable to a carbamate (C=O) stretch, formed via the absorption of CO$_2$. Similarly, after the absorption of CO$_2$, the $^{13}$C NMR of [$P_{66614}$][ImC] shows a new signal at 163.0 ppm, which can be attributed to a carbamate carbonyl carbon. Thus, the absorption mechanism of CO$_2$ by these ILs has been found herein to proceed by a reaction with the cyclic anion X$^-$. The anion-mediated reaction is exemplified in FIG. 2, which shows the formation of carbamate or carbonate bonds for [$P_{66614}$][Im], [$P_{66614}$][Oxa], and [$P_{66614}$][PhO] when these ILs are reacted with CO$_2$.

Figure 3:
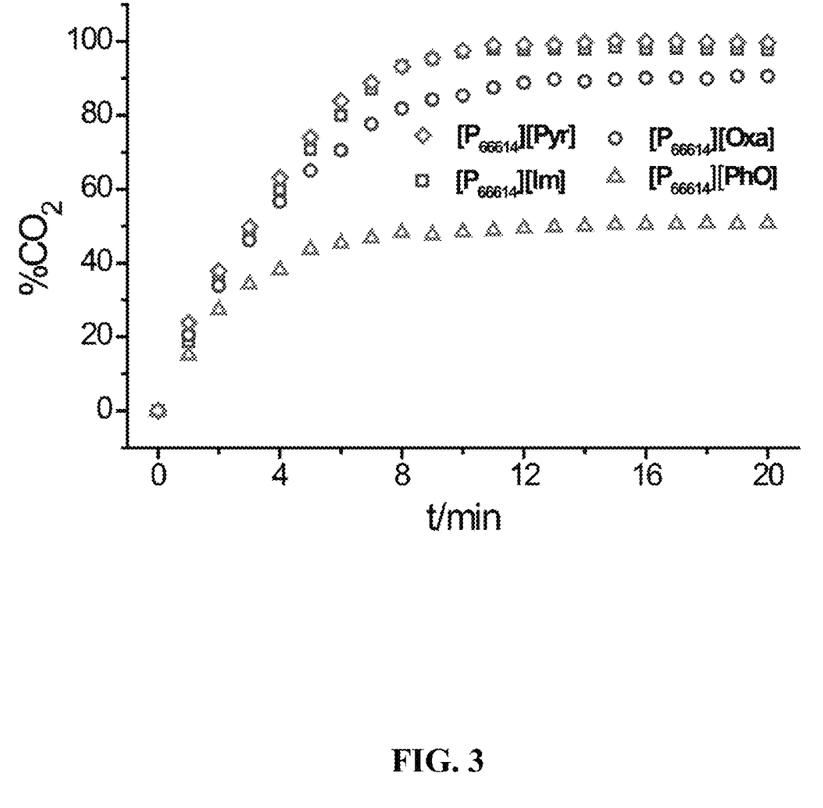
FIG. 3. Graph showing carbon dioxide absorption capacities for $[P_{66614}][Im]$, $[P_{66614}][Oxa]$, $[P_{66614}][Pyr]$, and $[P_{66614}][PhO]$ representative ionic liquids.

High absorption capacities (about 1 mol CO$_2$ per mole of IL) and rapid absorption rates were observed for these exemplary ILs. FIG. 3 shows the effect of different anions on CO$_2$ absorption. As shown by FIG. 3, an absorption capacity of 1.0, 0.98, and 0.91 mol CO$_2$ per mole of IL was achieved using [$P_{66614}$][Pyr], [$P_{66614}$][Im], and [$P_{66614}$][Oxa], respectively, while 0.50 mol CO$_2$ per mole of IL was achieved using [$P_{66614}$][PhO]. It is clear that the absorption capacity of CO$_2$ is significantly affected by the choice of anion in these ILs. Moreover, it has been found herein that the absorption capacity can be improved by use of an anion with a larger $pK_a$ because of its stronger reactivity to electrophilic gases, such as $CO_2$. Thus, by such judicious selection, a nearly equimolar $CO_2$ absorption can be achieved using the ILs described herein.

Figure 2:
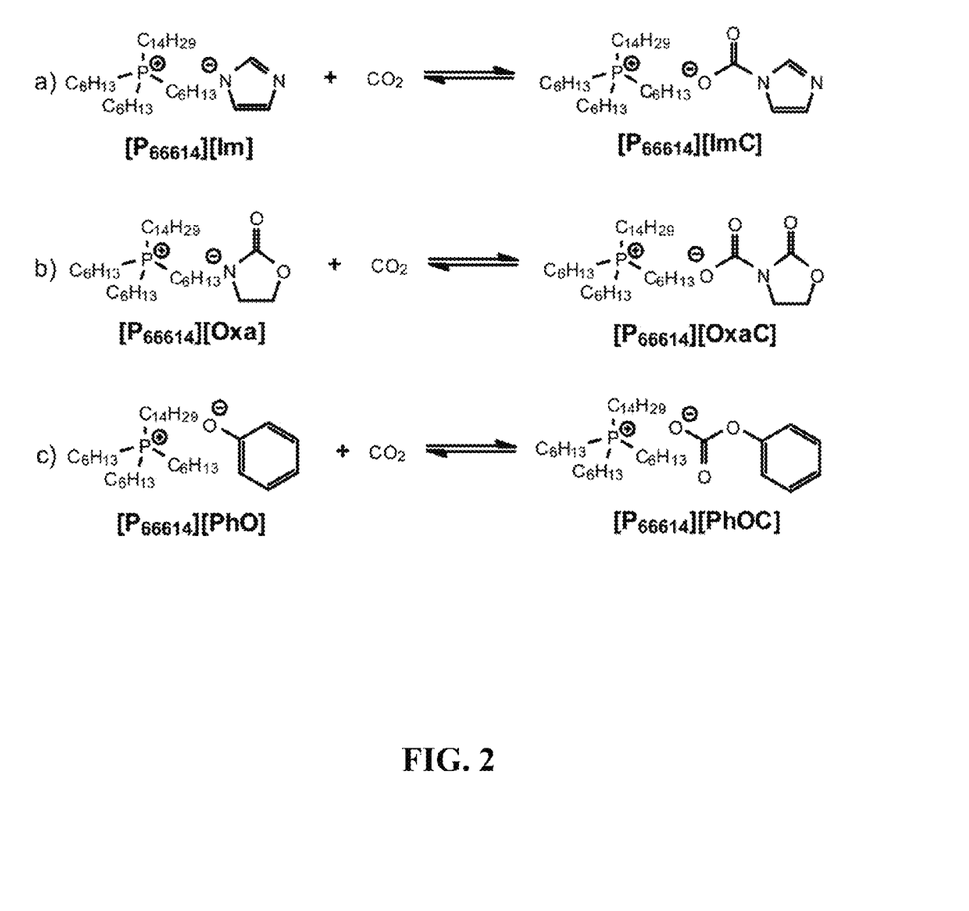
FIG. 2. Drawing showing the anion-centered $CO_2$ absorption mechanism found for $[P_{66614}][Im]$, $[P_{66614}][Oxa]$, and $[P_{66614}][PhO]$ representative ionic liquids.

Using gas-phase energy calculations, the energetics of reactions shown in FIG. 2 were obtained at the B3LYP/TZVP level of theory. Changes of energy for Pyr, Im, Oxa, and PhO were found to be −80.5, −85.2, −69.8, and −41.7 kJ/mol, respectively, which roughly agrees with the variation of the absorption capacities shown in FIG. 3.

The absorption rates of these exemplary ILs were found to be rapid. As shown by FIG. 3, $CO_2$ absorption is surprisingly almost complete in 10 minutes by each of these ILs. Without being bound by any theory, this rapid absorption is believed to be largely attributed to the ability of the instant ILs to substantially resist an increase in viscosity during $CO_2$ absorption. The viscosities of $[P_{66614}][Pyr]$, $[P_{66614}][Oxa]$, and $[P_{66614}][PhO]$, in particular, increased only to 555.1 cP, 1145.8 cP, and 645.4 cP, respectively, upon uptake of $CO_2$. These increases in viscosity are relatively minor, and thus, clearly show the ability of the instant ILs to maintain themselves as free-flowing liquids upon uptake of $CO_2$, in contrast to the general tendency of ILs of the art to form highly viscous gels or solids during absorption of $CO_2$. Remarkably, the viscosity of $[P_{66614}][Im]$ decreased from 810.4 cP to 648.7 cP upon uptake of $CO_2$. Without being bound by any theory, this unexpected decrease in viscosity may be a result of an absence of strong hydrogen-bond networks in $[P_{66614}][Im]$. Similarly, the substantial maintenance or slight increase in viscosity of other IL compositions described herein during $CO_2$ uptake may be attributed to the substantial reduction or elimination of hydrogen-bonding interactions during absorption as compared to IL compositions of the art.

The captured $CO_2$ was facilely stripped by heating or bubbling $N_2$ through the ILs. The reversibility of the absorption-and-release process exhibited by these ILs was demonstrated by TGA and IR analysis, as follows.

Figure 4:
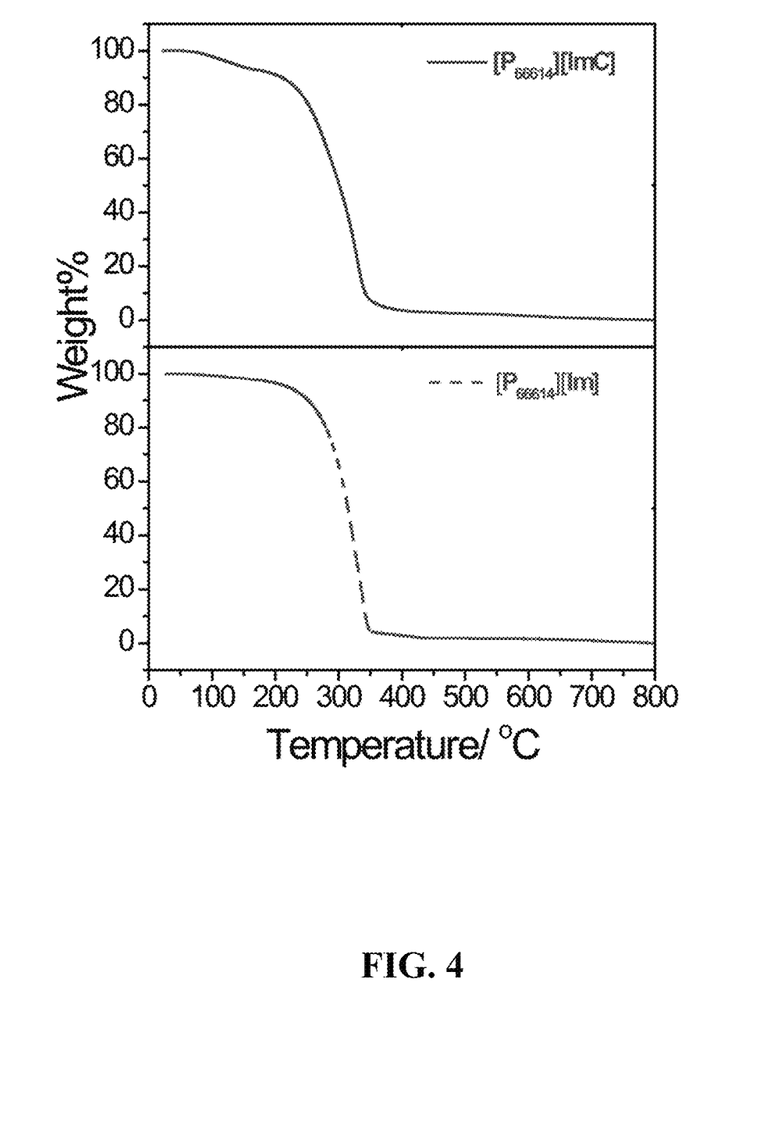
FIG. 4. Graphs comparing thermogravimetric analysis (TGA) plots for $[P_{66614}][Im]$ and $[P_{66614}][ImC]$ under a $N_2$ atmosphere and using a 10° C./min ramp rate.

FIG. 4 shows TGA plots comparing the decomposition characteristics of $[P_{66614}][Im]$ and $[P_{66614}][ImC]$. As shown by FIG. 4, the decomposition of $[P_{66614}][ImC]$ started when the temperature reached about 80° C. At 160° C., $[P_{66614}][ImC]$ lost about 7% of its mass, indicating that the release of $CO_2$ was almost complete.

Figure 5:
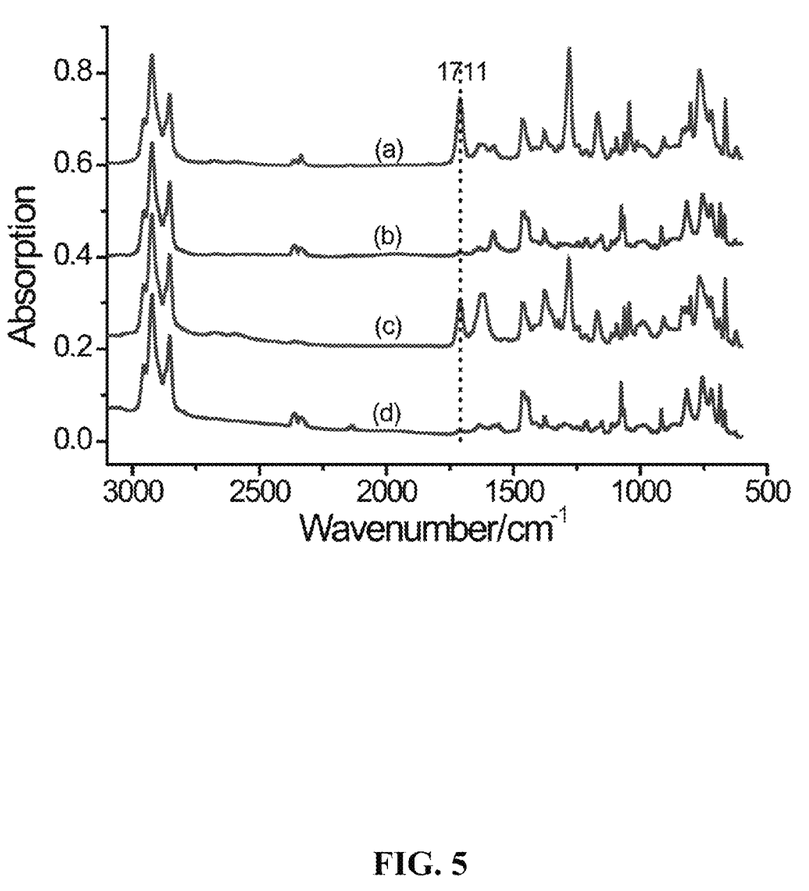
FIG. 5. Graph showing the $CO_2$ absorption and desorption (release) characteristics, as demonstrated by IR analysis, for: (a) fresh $[P_{66614}][Im]$, i.e., before any $CO_2$ absorption; (b) $[P_{66614}][ImC]$, after $CO_2$ absorption at 23° C.; (c) $[P_{66614}][Im]$, after heating at 100° C. for 1 hour; and (d) $[P_{66614}][ImC]$, after a second cycle of $CO_2$ absorption at 23° C.

FIG. 5 shows the results of an IR study on two cycles of absorption and desorption (release) of $CO_2$ for $[P_{66614}][ImC]$. As shown in FIG. 5, IR spectra were obtained for $[P_{66614}][Im]$ before the absorption of $CO_2$ (plot (d)), after the absorption of $CO_2$ to produce $[P_{66614}][ImC]$ at 23° C. (plot (c)), after heating $[P_{66614}][ImC]$ of plot (c) for 1 hour at 100° C. under bubbling $N_2$ to release $CO_2$ to reproduce $[P_{66614}][Im]$ (plot (b)), and after the re-absorption of $CO_2$ at 23° C. to reproduce $[P_{66614}][ImC]$ (plot (a)). As shown by FIG. 5, the peak at 1711 cm$^{-1}$, attributed to a carbamate (C=O) stretch, was visible upon capture of $CO_2$ by $[P_{66614}][Im]$, while this peak disappeared after stripping at 100° C. under bubbling $N_2$. This absorption-and-release result demonstrates that the process of $CO_2$ capture by ILs of Formula (1) is highly reversible, and that ILs of Formula (1) can be recycled and re-used by virtue of this characteristic.

While there have been shown and described what are at present considered the preferred embodiments of the invention, those skilled in the art may make various changes and modifications which remain within the scope of the invention defined by the appended claims.

What is claimed is:

1. An ionic liquid composition having the following chemical structural formula:

wherein $R^1$, $R^2$, $R^3$, and $R^4$ are independently selected from hydrocarbon groups containing at least 1 and up to 20 carbon atoms, wherein at least one of $R^1$, $R^2$, $R^3$, and $R^4$ is an alkyl or alkenyl group, provided that at least one of $R^1$, $R^2$, $R^3$, and $R^4$ contains at least four more carbon atoms than another of $R^1$, $R^2$, $R^3$, and $R^4$; and $X^-$ is a deprotonated phenolic or thiophenolic anion reactive with carbon dioxide or sulfur dioxide.

2. The ionic liquid composition of claim 1, wherein $R^1$, $R^2$, $R^3$, and $R^4$ contain at least 3 and up to 20 carbon atoms.

3. The ionic liquid composition of claim 1, wherein $R^1$, $R^2$, $R^3$, and $R^4$ contain at least 4 and up to 20 carbon atoms.

4. The ionic liquid composition of claim 1, wherein $R^1$, $R^2$, $R^3$, and $R^4$ contain at least 5 and up to 20 carbon atoms.

5. The ionic liquid composition of claim 1, wherein $R^1$, $R^2$, $R^3$, and $R^4$ contain at least 6 and up to 20 carbon atoms.

6. The ionic liquid composition of claim 1, wherein at least two of $R^1$, $R^2$, $R^3$, and $R^4$ are alkyl groups.

7. The ionic liquid composition of claim 1, wherein said hydrocarbon groups are alkyl groups.

8. The ionic liquid composition of claim 1, wherein at least two of $R^1$, $R^2$, $R^3$, and $R^4$ are not equivalent.

9. The ionic liquid composition of claim 1, wherein at least one of $R^1$, $R^2$, $R^3$, and $R^4$ contains at least five more carbon atoms than another of $R^1$, $R^2$, $R^3$, and $R^4$.

10. The ionic liquid composition of claim 1, wherein at least one of $R^1$, $R^2$, $R^3$, and $R^4$ contains at least six more carbon atoms than another of $R^1$, $R^2$, $R^3$, and $R^4$.

11. The ionic liquid composition of claim 1, wherein said deprotonated phenolic or thiophenolic anion does not possess a carboxylate substituent.

12. The ionic liquid composition of claim 1, wherein said deprotonated phenolic or thiophenolic anion is not an amino acid.

13. The ionic liquid composition of claim 1, wherein said ionic liquid possesses a viscosity of no more than 2000 cP at 25° C.

14. The ionic liquid composition of claim 1, wherein said ionic liquid possesses a viscosity of no more than 1500 cP at 25° C.

15. The ionic liquid composition of claim 1, wherein said ionic liquid possesses a viscosity of no more than 1000 cP at 25° C.

16. The ionic liquid composition of claim 1, wherein said ionic liquid possesses a decomposition temperature of at least 150° C.

17. The ionic liquid composition of claim 1, wherein said ionic liquid possesses a $CO_2$ absorption capacity of at least 0.7 moles $CO_2$ per mole of ionic liquid.

18. The ionic liquid composition of claim 1, wherein said ionic liquid possesses a $CO_2$ absorption capacity of at least 0.8 moles $CO_2$ per mole of ionic liquid.

19. The ionic liquid composition of claim 1, wherein said ionic liquid possesses a $CO_2$ absorption capacity of at least 0.9 moles $CO_2$ per mole of ionic liquid.

20. A method for capturing a gaseous electrophilic species, the method comprising contacting said gaseous electrophilic species with an ionic liquid according to claim 1.

21. The method according to claim 20, further comprising removing captured electrophilic gas from said ionic liquid to produce fresh ionic liquid, and re-using said fresh ionic liquid for capturing additional electrophilic gas.

22. A method for capturing gaseous carbon dioxide, the method comprising contacting said carbon dioxide with an ionic liquid according to claim 1.

23. The method according to claim 22, wherein the carbon dioxide is nucleophilicly attacked by the deprotonated phenolic or thiophenolic anion.

24. The method according to claim 22, wherein the carbon dioxide is not protonated during the reaction.

25. The method according to claim 22, wherein said method for capturing gaseous carbon dioxide is integrated with a process that produces carbon dioxide as a byproduct.

26. The method according to claim 25, wherein said process that produces carbon dioxide as a byproduct is a combustion process.

27. A method for capturing atmospheric sulfur dioxide, the method comprising contacting said sulfur dioxide with an ionic liquid according to claim 1.

28. The method according to claim 27, wherein the sulfur dioxide is nucleophilicly attacked by the deprotonated phenolic or thiophenolic anion.

29. The method according to claim 27, wherein the sulfur dioxide is not protonated during the reaction.

30. The method according to claim 27, wherein said method for capturing atmospheric sulfur dioxide is integrated with a process that produces sulfur dioxide as a byproduct.

31. The method according to claim 30, wherein said process that produces sulfur dioxide as a byproduct is a combustion process.

32. The method of claim 31, wherein said combustion process is a coal-powered process.

33. An ionic liquid composition having the following chemical structural formula:

(1)

wherein $R^1$, $R^2$, $R^3$, and $R^4$ are independently selected from hydrocarbon groups containing at least 1 and up to 20 carbon atoms, provided that at least one of $R^1$, $R^2$, $R^3$, and $R^4$ contains at least four more carbon atoms than another of $R^1$, $R^2$, $R^3$, and $R^4$; and $X^-$ is a deprotonated phenolic or thiophenolic anion reactive with carbon dioxide or sulfur dioxide.

34. A method for capturing a gaseous electrophilic species, the method comprising contacting said gaseous electrophilic species with an ionic liquid according to claim 33.

35. The method of claim 34, wherein the gaseous electrophilic species is carbon dioxide or sulfur dioxide.

\* \* \* \* \*